US010972705B2

(12) United States Patent
Tsuchiya et al.

(10) Patent No.: US 10,972,705 B2
(45) Date of Patent: Apr. 6, 2021

(54) MEDICAL DISPLAY APPARATUS, ENDOSCOPIC SURGERY SYSTEM, AND METHOD OF DISPLAYING MEDICAL IMAGE

(71) Applicant: OLYMPUS CORPORATION, Tokyo (JP)

(72) Inventors: Shusuke Tsuchiya, Akishima (JP); Masaya Fujita, Sagamihara (JP); Masahiro Kudo, Hino (JP); Takayuki Ida, Machida (JP); Shinya Moriyama, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/722,602

(22) Filed: Dec. 20, 2019

(65) Prior Publication Data

US 2020/0128214 A1 Apr. 23, 2020

Related U.S. Application Data

(63) Continuation of application No. PCT/JP2018/014745, filed on Apr. 6, 2018.

(30) Foreign Application Priority Data

Jun. 20, 2017 (JP) .............................. JP2017-120805

(51) Int. Cl.
*H04N 7/18* (2006.01)
*A61B 1/00* (2006.01)
(Continued)

(52) U.S. Cl.
CPC ........... *H04N 7/181* (2013.01); *A61B 1/0005* (2013.01); *A61B 1/00009* (2013.01); *A61B 1/00048* (2013.01); *A61B 1/04* (2013.01)

(58) Field of Classification Search
CPC .............. A61B 1/00009; A61B 1/0005; A61B 1/00048; A61B 1/04; A61B 1/045; H04N 7/181
(Continued)

(56) References Cited

U.S. PATENT DOCUMENTS 4,667,229 A * 5/1987 Cooper .................. H04N 9/045
348/249
2009/0043163 A1 2/2009 Ozaki
(Continued)

FOREIGN PATENT DOCUMENTS

EP 2031529 A2 3/2009
JP H05-176881 A 7/1993
(Continued)

OTHER PUBLICATIONS

Jul. 3, 2018 International Search Report issued in International Patent Application No. PCT/JP2018/014745.

*Primary Examiner* — Susan E. Hodges
(74) *Attorney, Agent, or Firm* — Oliff PLC

(57) ABSTRACT

A medical display apparatus includes: a display unit configured to display an endoscope image; at least one video signal input circuit to which video signals related to the endoscope image can be inputted from an external medical instrument; a video processing circuit configured to generate a video reflecting a display setting specified for each of the video signals; and first and second processors, the first processor determines an endoscope type based on a mask pattern of the endoscope image related to each of the inputted video signals, and the second processor designates a display set value for each of video signals related to different endoscope images to the video processing circuit according to a determination result.

7 Claims, 8 Drawing Sheets

(51) Int. Cl.
*G06T 7/00* (2017.01)
*G06K 9/46* (2006.01)
*A61B 1/04* (2006.01)

(58) Field of Classification Search
USPC .......................................................... 348/65
See application file for complete search history.

(56) References Cited

U.S. PATENT DOCUMENTS

| | | | | |
|---|---|---|---|---|
| 2012/0201433 | A1* | 8/2012 | Iwasaki | A61B 1/00009 |
| | | | | 382/128 |
| 2012/0299967 | A1* | 11/2012 | Urabe | G09G 5/14 |
| | | | | 345/660 |
| 2016/0054969 | A1* | 2/2016 | Maruyama | G09G 3/2003 |
| | | | | 345/690 |
| 2016/0128546 | A1* | 5/2016 | Fujita | A61B 1/04 |
| | | | | 600/103 |
| 2019/0328208 | A1* | 10/2019 | Kashima | A61B 1/00009 |

FOREIGN PATENT DOCUMENTS

| | | |
|---|---|---|
| JP | 2004-240108 A | 8/2004 |
| JP | 2009-039431 A | 2/2009 |
| JP | 2009-044400 A | 2/2009 |
| JP | 2010-000185 A | 1/2010 |
| WO | 2016/190393 A1 | 12/2016 |

\* cited by examiner

FIG. 6

| | INTERPRETATION IMAGE | FIRST SURGICAL ENDOSCOPE | SECOND SURGICAL ENDOSCOPE | FIRST GASTROINTESTINAL ENDOSCOPE | SECOND GASTROINTESTINAL ENDOSCOPE |
|---|---|---|---|---|---|
| SCAN SIZE | OFF | OFF | MODE 1 | OFF | MODE 2 |
| COLOR TEMPERATURE | D65 | D65 | D65 | D93 | D93 |
| GAMMA | DICOM | Endoscope1 | Endoscope1 | Endoscope2 | Endoscope2 |
| PHASE | 50 | 50 | 50 | 50 | 50 |
| CHROMA | 50 | 50 | 50 | 50 | 50 |
| CONTRAST | 70 | 50 | 50 | 50 | 50 |
| BRIGHTNESS | 80 | 80 | 80 | 80 | 80 |
| ... | ... | ... | ... | ... | |

MEDICAL DISPLAY APPARATUS, ENDOSCOPIC SURGERY SYSTEM, AND METHOD OF DISPLAYING MEDICAL IMAGE

CROSS REFERENCE TO RELATED APPLICATION

This application is a continuation application of PCT/JP2018/014745 filed on Apr. 6, 2018 and claims benefit of Japanese Application No. 2017-120805 filed in Japan on Jun. 20, 2017, the entire contents of which are incorporated herein by this reference.

BACKGROUND

In recent years, a medical system such as an endoscopic surgery system, which performs the procedure using an endoscope, has become widespread, and various medical instruments have been also used. For example, as a medical system disposed in a surgery room, an endoscopic surgery system has been known in which a cart equipped with various medical instruments such as an endoscopic camera apparatus to which an endoscope is connected, a light source apparatus, and an image recording apparatus is placed and a display apparatus such as a monitor configured to display an endoscope image is arranged.

In the endoscopic surgery system described above, a system has recently been known in which, during endoscopic surgery, a monitor displays video signals related to multiple types of medical modalities depending on the procedure, for example, video signals such as surgical endoscope images, gastrointestinal endoscope images, or interpretation video images related to multiple types of endoscopes.

In such an endoscopic surgery system, a monitor, which can individually store various set values (for example, scan size, color temperature, and gamma characteristic) for each input terminal, has been proposed in view of the above-described applications. For example, as the monitor described above, a monitor has also been known which is provided with input terminals corresponding to multiple types of medical modalities, performs an appropriate setting on each of video signals related to the medical modalities inputted to the respective input terminals, and then displays the video signals.

On the other hand, in recent years, an integration facility has been proposed in which video routing is performed by a switcher. In such an integration facility, a system has also been known in which a video signal inputted to a single input terminal arranged on a monitor is switched by the switcher. In other words, video signals related to multiple types of medical modalities can be switched and displayed in the system even when the monitor includes only the single input terminal.

Here, the video signals related to multiple types of medical modalities may be different in appropriate values of various set values (for example, scan size, color temperature, and gamma characteristic) from each other. However, in the case of the system in which the video signal inputted to the single input terminal is switched by the switcher as described above, the video signal to be inputted to the monitor is changed by the switcher, while the video signal has not been changed to an appropriate set value for each of the medical modalities on the monitor side.

To resolve this issue, in a monitor provided with one input terminal to which various video signals can be inputted, when a predetermined video signal is inputted to the input terminal, a difference in video format (resolution) of the video signal can be determined and a display setting related to the video signal inputted to the input terminal can be changed according to the type of the video format (resolution).

In recent years, images having a resolution of a so-called full HD (1920×1080) have become mainstream, and video signals of the same format have been increasing even in different medical modalities.

Here, various operations are required to display an appropriate color on a monitor that displays an endoscope image in endoscopic surgery, but an example of a monitor operation will be described hereinafter according to surgery scenes.

(1) Before the surgery starts, an interpretation image photographed before the surgery is confirmed on the monitor to confirm a target region in advance, but a change of gamma is required at this time. Further, a monochrome image may be confirmed by being changed in a manner easily recognizable with contrast or brightness by a user.

(2) When the surgery starts, for example, a surgical endoscope is displayed on the monitor. At this time, since the interpretation image is displayed on the monitor as in (1) described above, the gamma should be returned to the original state, and a scan size should be changed according to a processor to be used. In addition, when contrast or brightness is changed in (1), the contrast or brightness should be also returned to the original state.

(3) When a resection site approaches, the interpretation image may be displayed again on the monitor to confirm a location of a tumor. At this time, a setting is necessary to be returned to the setting of (1) again. On the other hand, in a case of returning to the surgical endoscope, the setting of (2) needs to be performed again.

(4) Depending on the procedure, a gastrointestinal endoscope may be used to check leaks after anastomosis. In other words, when a surgical endoscope video (see (2) described above) is switched to a gastrointestinal endoscope video, a change of scan size is required. Further, a change of color temperature may be required.

(5) In a final closing, the surgical endoscope video is displayed in many cases, but the change of scan size or color temperature may be required even in this case.

As described above, video signals from various medical modalities are displayed on the monitors, which display the endoscope image according to the surgical scenes.

SUMMARY

This application relates to a medical display apparatus, an endoscopic surgery system, and a method of displaying a medical image, and particularly to a medical display apparatus capable of inputting multiple types of video signals to the same input terminal, an endoscopic surgery system, and a method of displaying a medical image.

A medical display apparatus can include: a display unit configured to display an endoscope image; at least one video signal input circuit to which video signals related to the endoscope image can be inputted from an external medical instrument; a video processing circuit configured to generate a video reflecting a display setting specified for each of the video signals; and first and second processors, the first processor determines an endoscope type based on a mask pattern of the endoscope image related to each of the inputted video signals, and the second processor designates a display set value for each of video images related to different endoscope images to the video processing circuit according to a determination result.

An endoscopic surgery system can include: a controlled instrument configured of a plurality of medical instruments; and a medical display apparatus, the medical display apparatus including: a display unit configured to display an endoscope image; at least one video signal input circuit to which video signals related to the endoscope image can be inputted from an external medical instrument; a first processor configured to determine whether the video signals inputted to the video signal input circuit are either color video signals or monochrome video signals; a second processor configured to determine an endoscope type based on a mask pattern of an endoscope image related to each of the video signals when the video signals are the color video signals based on a determination result in the first processor; a video processing circuit configured to generate a video reflecting a display setting for each of the determined video signals, according to determination results of the first and second processors; and a third processor configured to designate a display set value for each of video images related to different endoscope images to the video processing circuit, according to the determination results of the first and second processors.

A method of displaying a medical image according to an aspect of the present invention includes: performing a first determination of determining whether video signals related to an endoscope image among video signals inputted to a video signal input circuit from an external medical instrument are either color video signals or monochrome video signals; performing a second determination of determining an endoscope type based on a mask size of an endoscope image related to each of the video signals when the video signals are the color video signals based on a result of the first determination; and generating a video reflecting a display setting for each of the determined video signals, according to results of the first and second determinations.

BRIEF DESCRIPTION OF THE DRAWINGS

FIG. 6 is a table showing information stored in a setting storage section in the medical display apparatus of an exemplary embodiment;

DETAILED DESCRIPTION

Exemplary embodiments will be described below with reference to the drawings.

Figure 1:
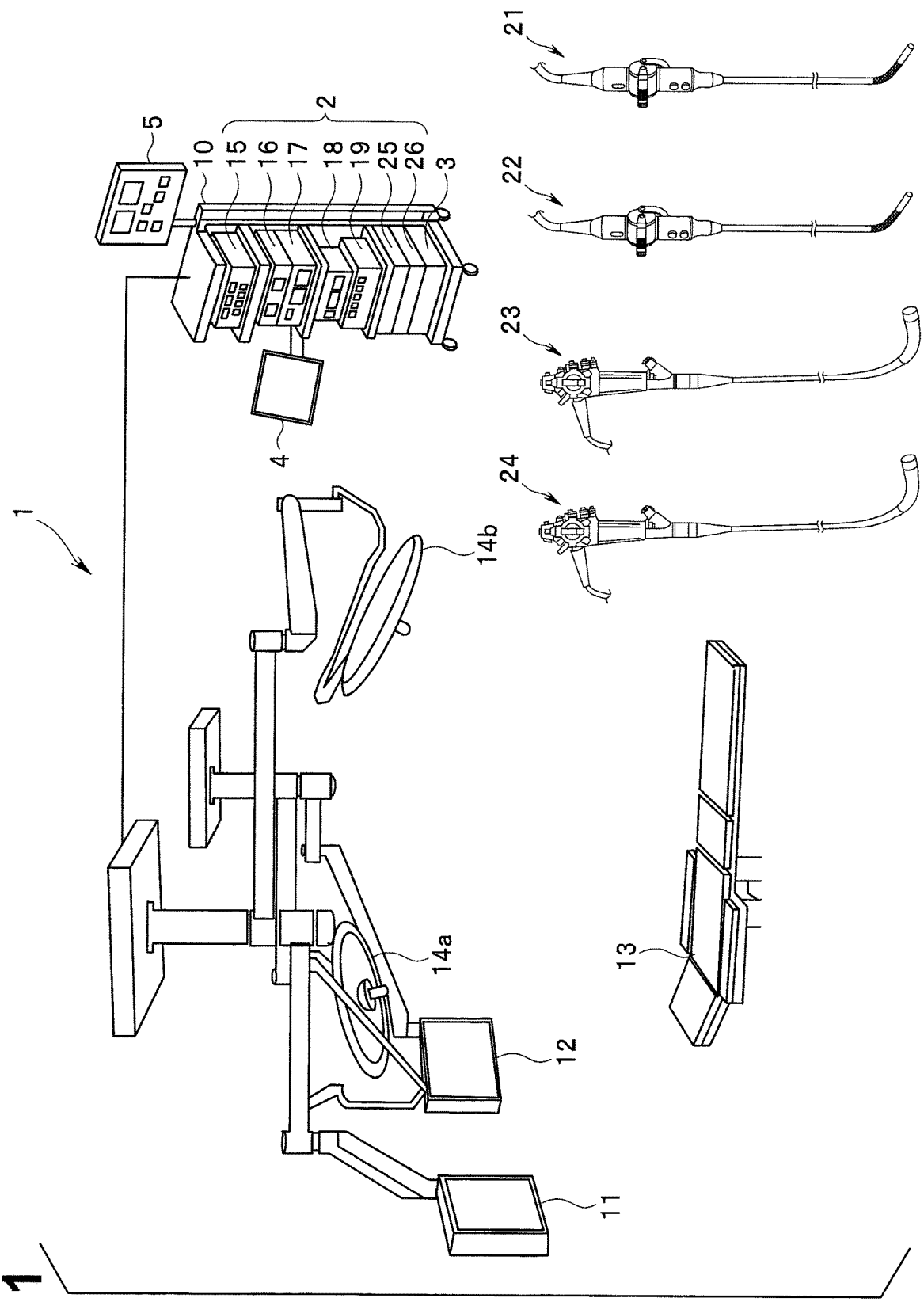
FIG. 1 is a diagram showing an overall configuration of an endoscopic surgery system including a medical display apparatus of an exemplary embodiment.
Figure 2:
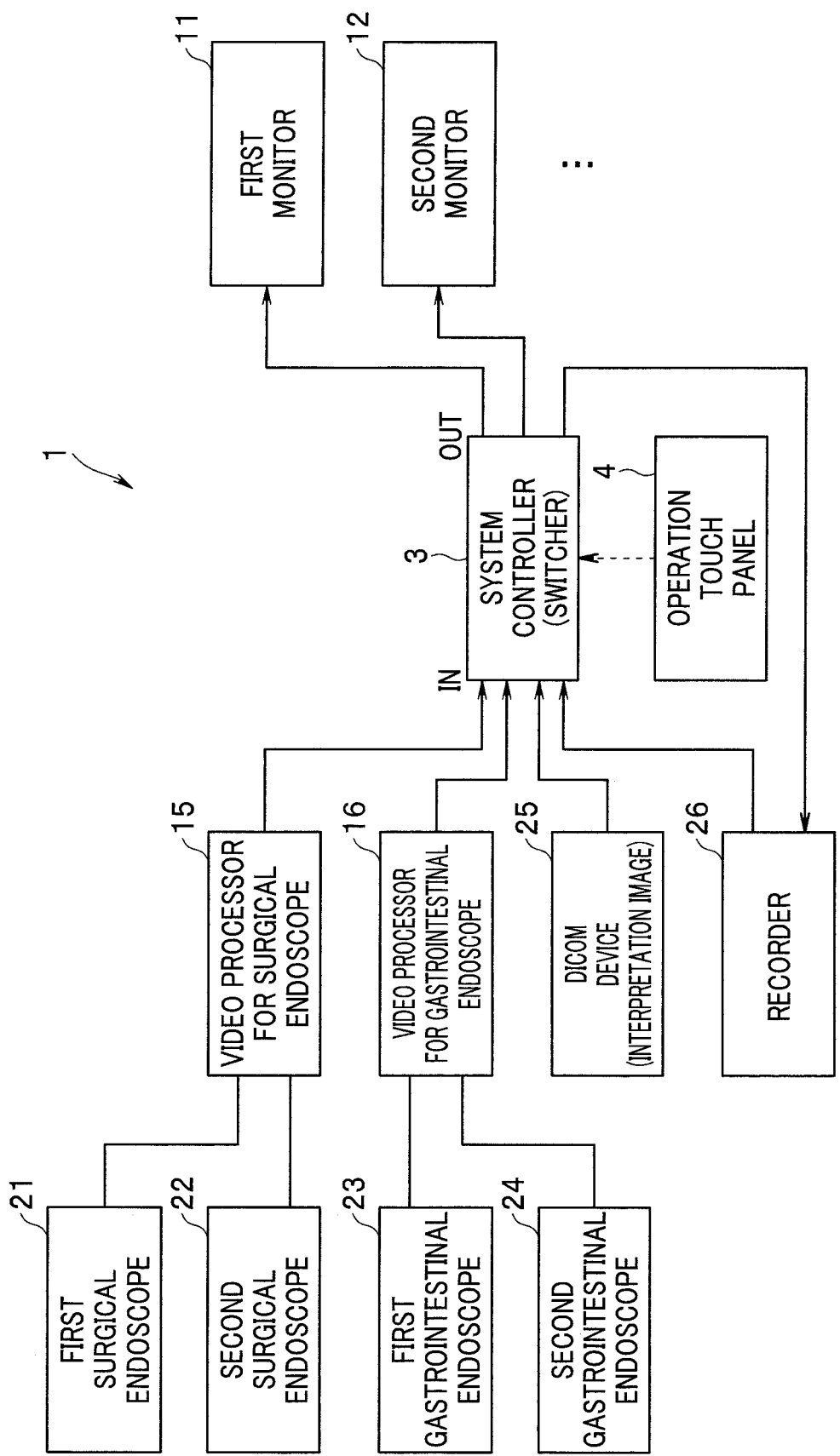
FIG. 2 is a block diagram showing an electrical configuration of main components in the endoscopic surgery system according to an exemplary embodiment.

FIG. 1 is a diagram showing an overall configuration of an endoscopic surgery system including a medical display apparatus of a an exemplary embodiment, and FIG. 2 is a block diagram showing an electrical configuration of main components in the endoscopic surgery system according to an exemplary embodiment.

As shown in FIG. 1, an endoscopic surgery system 1 according to an exemplary embodiment is, for example, a medical system disposed in a surgery room, and includes a medical instrument group 2 that is a controlled instrument including a plurality of medical instruments, a system controller 3 that performs centralized control on various medical instruments in the medical instrument group 2 and a monitor group to be described below, an operation panel 4 that receives various operations from an operator such as a nurse, and a display panel 5 that displays predetermined information such as various operation statuses.

The endoscopic surgery system 1 also includes permanent facilities in the surgery room, for example, a cart 10 mounted with, for example, the medical instrument group 2 and the system controller 3 which are described above, a plurality of monitors (first monitor 11 and second monitor 12) that hang from a ceiling to display an endoscope image under control of the system controller 3, a patient bed 13 on which a patient lies, and a shadowless light (shadowless light 14a, shadowless light 14b) that hangs from the ceiling and is controlled by the same system controller 3.

The medical instrument group 2 described above in the present embodiment includes not only medical instruments such as a camera apparatus for endoscope 15, a video processor 16, a light source apparatus 17, a pneumoperitoneum apparatus 18, and an electrocautery apparatus 19, but also medical instruments such as a DICOM device 25 for interpretation image as a medical modality and a recorder 26, and all the components of the medical instrument group 2 are mounted on the cart 10 as shown in FIG. 1.

Further, the endoscopic surgery system 1 of the present embodiment includes a plurality of endoscopes (a first surgical endoscope 21, a second surgical endoscope 22, a first gastrointestinal endoscope 23, and a second gastrointestinal endoscope 24 in the present embodiment) that are connectable to the video processor for surgical endoscope 15 or the video processor for gastrointestinal endoscope 16 among the controlled instruments described above and serve as a medical modality.

The video processor for surgical endoscope 15 is configured such that the first surgical endoscope 21 and the second surgical endoscope 22 are connected via predetermined cords (not shown) and such that an image-pickup signal related to an endoscope image is inputted from the first surgical endoscope 21 or the second surgical endoscope 22.

The video processor for surgical endoscope 15 performs predetermined signal processing on the image-pickup signal related to the inputted surgical endoscope image to generate a video signal, and outputs the video signal to the system controller 3.

On the other hand, the video processor for gastrointestinal endoscope 16 is configured such that the first gastrointestinal endoscope 23 and the second gastrointestinal endoscope 24 are connected via universal cords (not shown) and such that an image-pickup signal related to an endoscope image is inputted from the first gastrointestinal endoscope 23 or the second gastrointestinal endoscope 24.

The video processor for gastrointestinal endoscope 16 performs predetermined signal processing on the image-pickup signal related to the inputted gastrointestinal endoscope image to generate a video signal, and outputs the video signal to the system controller 3.

In other words, as described above in the present embodiment, the image-pickup signal is inputted from the plurality of endoscopes, that is, the first surgical endoscope 21, the second surgical endoscope 22, the first gastrointestinal endoscope 23, or the second gastrointestinal endoscope 24 to the video processor for surgical endoscope 15 or the video processor for gastrointestinal endoscope 16, and the image-pickup signal is subjected to the predetermined signal processing in the video processor for surgical endoscope 15 or the video processor for gastrointestinal endoscope 16 and is then inputted to the system controller 3 in a form of the video signal (see FIG. 2).

The light source apparatus 17 includes a light source portion that generates predetermined illumination light, and supplies the illumination light to the respective endoscopes described above via a light guide cable provided in a universal cord (not shown).

In addition, a carbon dioxide cylinder (not shown) is connected to the pneumoperitoneum apparatus 18, and is configured to supply carbon dioxide into patient's abdomen from the pneumoperitoneum apparatus 18 through a pneumoperitoneum tube extending from a patient (not shown). Furthermore, the electrocautery apparatus 19 can supply electric power to an electrocautery (not shown) to drive the electrocautery.

The operation panel 4 is, for example, a touch panel display in which a liquid crystal display and a touch panel sensor layered on the liquid crystal display are integrally configured. The operation panel 4 is an operation apparatus through which the medical instrument group 2 is operated by a nurse or the like in a non-sterilized region, and operation information is inputted to the system controller 3 (see FIG. 2). The display panel 5 is a display apparatus that can allow all data to be selectively displayed during surgery.

<Surgical Endoscope and Gastrointestinal Endoscope>

As described above, the endoscopic surgery system 1 according to an exemplary embodiment includes, as the medical modality related to the endoscope image, surgical endoscopes such as the first surgical endoscope 21 and the second surgical endoscope 22 and gastrointestinal endoscopes such as the first gastrointestinal endoscope 23 and the second gastrointestinal endoscope 24. The image-pickup signals related to the endoscope images outputted from these endoscopes are inputted to the video processor for surgical endoscope 15 or the video processor for gastrointestinal endoscope 16, as described above.

Both of the first surgical endoscope 21 and the second surgical endoscope 22 are known surgical endoscopes, but the first surgical endoscope 21 and the second surgical endoscope 22 have different mask patterns related to the endoscope images. On the other hand, both of the first surgical endoscope 21 and the second surgical endoscope 22 output image-pickup signals having the same video format (resolution).

In addition, both of the first gastrointestinal endoscope 23 and the second gastrointestinal endoscope 24 are also known gastrointestinal endoscopes, but, as in the above description, the first gastrointestinal endoscope 23 and the second gastrointestinal endoscope 24 have different mask patterns related to the endoscope images. On the other hand, as in the above description, each of the first gastrointestinal endoscope 23 and the second gastrointestinal endoscope 24 outputs an image-pickup signal having the same video format (resolution).

Further, each of the first surgical endoscope 21, the second surgical endoscope 22, the first gastrointestinal endoscope 23, and the second gastrointestinal endoscope 24 outputs an image-pickup signal having the same resolution.

Note that as described above, the image-pickup signals inputted from the first surgical endoscope 21, the second surgical endoscope 22, the first gastrointestinal endoscope 23, and the second gastrointestinal endoscope 24 are subjected to predetermined image processing in the video processor for surgical endoscope 15 or the video processor for gastrointestinal endoscope 16 and are then inputted to the system controller 3 in a form of the video signal (see FIG. 2).

<DICOM Device and Recorder>

As described above, the endoscopic surgery system 1 according to an exemplary embodiment includes the DICOM device 25 and the recorder 26 as the medical modality related to the endoscope image.

The DICOM device 25 is a device that records and outputs a video signal related to an endoscope image (interpretation image) having a medical image format called a so-called DICOM standard (digital imaging and communication in medicine).

A video signal related to the endoscope image (interpretation image) recorded and outputted by the DICOM device 25 has a gamma characteristic conforming to the DICOM standard, and differs from the video signals outputted from any of the first surgical endoscope 21, the second surgical endoscope 22, the first gastrointestinal endoscope 23, and the second gastrointestinal endoscope 24 described above. On the other hand, the video signal related to the endoscope image (interpretation image) of the DICOM device 25 is set to an image-pickup signal having the same video format (resolution) as in the respective endoscopes described above.

The recorder 26 is a known recording device for endoscope images, but enables the images to record with a display setting different from the display setting of any of the first surgical endoscope 21, the second surgical endoscope 22, the first gastrointestinal endoscope 23, and the second gastrointestinal endoscope 24 described above. A video signal related to the recorded image is set to an image-pickup signal having the same video format (resolution) as in the respective endoscopes described above.

Note that the outputted signals of the DICOM device 25 and the recorder 26 are both inputted to the system controller 3 (see FIG. 2).

<System Controller 3>

As described above, the system controller 3 is connected to not only various medical instruments related to the medical instrument group 2 including, for example, the video processor for surgical endoscope 15, the video processor for gastrointestinal endoscope 16, the DICOM device 25, and the recorder 26 but also monitors such as a first monitor 11 and a second monitor 12, and controls these components.

Further, the system controller 3 serves as a switcher configured to input and route, to the first monitor 11 or the second monitor 12, the video signal related to the endoscope image inputted from the first surgical endoscope 21, the second surgical endoscope 22, the first gastrointestinal endoscope 23, and the second gastrointestinal endoscope 24 as the medical modality related to the endoscope image and the video signal related to the endoscope image inputted from the DICOM device 25 and the recorder 26 via the video processor for surgical endoscope 15 or the video processor for gastrointestinal endoscope 16.

<First Monitor 11 and Second Monitor 12>

Each of the first monitor 11 and the second monitor 12 displays, as a predetermined endoscope image, the video signal inputted and routed appropriately by the system controller 3 serving as the switcher described above, under control of the system controller 3.

An internal configuration of the first monitor 11 and the second monitor 12 will be described below with reference to FIG. 4. Since the first monitor 11 and the second monitor 12 have the same configuration, the internal configuration of the first monitor 11 will be shown in FIG. 4 as an example.

Before describing the internal configuration of the first monitor 11 (the second monitor 12), a conventional monitor will be described below with reference to FIG. 3.

Figure 3:
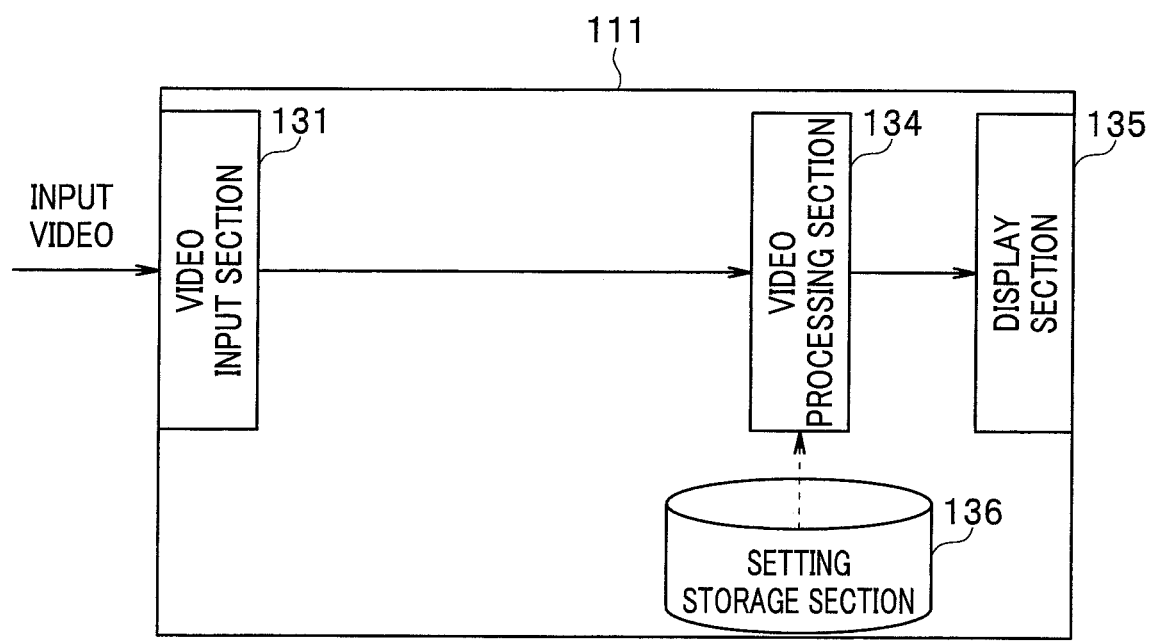
FIG. 3 is a block diagram showing an example of an electrical configuration in a conventional medical display apparatus.
Figure 4:
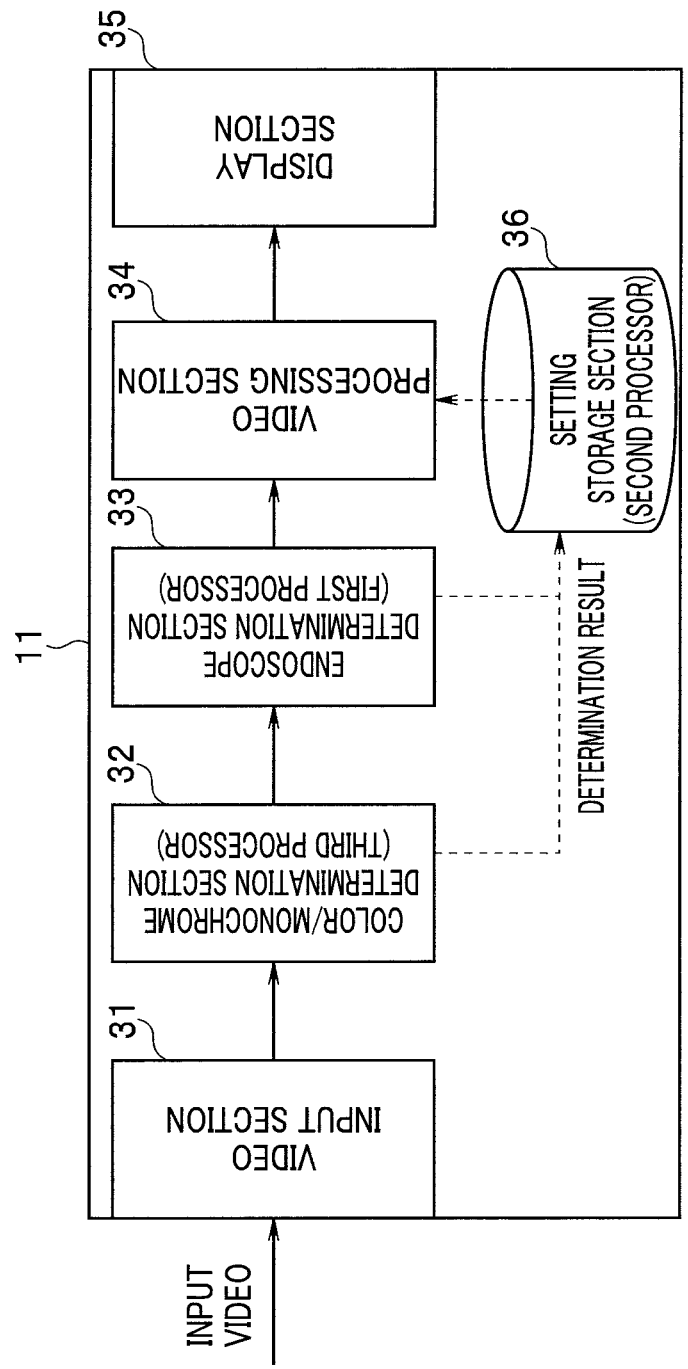
FIG. 4 is a block diagram showing an electrical configuration in the medical display apparatus of an exemplary embodiment.

FIG. 3 is a block diagram showing an example of an electrical configuration in a conventional medical display apparatus, and FIG. 4 is a block diagram showing an electrical configuration in the medical display apparatus (the first monitor 11 or the second monitor 12).

In a conventional monitor 111, as shown in FIG. 3, a video processing section 134 performs video processing on a video signal inputted to an input terminal, which is a video input section 131, according to a preset set value stored in a setting storage section 136, and the video signal is only displayed on a display section 135.

On the other hand, as shown in FIG. 4, the first monitor 11 (the second monitor 12) includes: a display section 35 that is a display unit configured to display an endoscope image; a single video signal input section 31 to which a video signal related to an endoscope image can be inputted from the external medical instrument; a video signal determination section (color/monochrome determination section) 32 that determines the video signal inputted to the video signal input section 31; an endoscope determination section 33 that determines an endoscope type based on the determination result of the color/monochrome determination section 32; a setting storage section 36 capable of setting a set value for each of video signals related to different endoscope images; and a video processing section 34 that generates a video obtained by reflecting the setting of the setting storage section 36 for each of the determined video signals, according to the determination results of the color/monochrome determination section 32 and the endoscope determination section 33.

In the present embodiment, the video signal input section 31 is configured of a video signal input circuit including a single input terminal through which a video signal can be inputted, and is configured to input the endoscope image routed appropriately by the switcher function in the system controller 3.

The video signal input section 31 has a function of detecting that the video signal is inputted, and also detects whether the inputted video signal is switched by the switcher function in the system controller 3.

The color/monochrome determination section 32 has a function of determining whether the video signal inputted to the video signal input section (the input terminal) 31 is either a color video signal or a monochrome video signal. In other words, the color/monochrome determination section 32 determines whether the video signal inputted to the video signal input section 31 is a color video signal related to the image-pickup signal inputted from the endoscopes, for example, the first surgical endoscope 21, the second surgical endoscope 22, the first gastrointestinal endoscope 23, and the second gastrointestinal endoscope 24 or a monochrome video signal related to the interpretation image in the DICOM device 25.

When the color/monochrome determination section 32 determines that the video signal is the color video signal based on the determination result, the endoscope determination section 33 recognizes that the video signal inputted to the video signal input section 31 is the video signal related to the image-pickup signal inputted from any one of the endoscopes, for example, the first surgical endoscope 21, the second surgical endoscope 22, the first gastrointestinal endoscope 23, and the second gastrointestinal endoscope 24 and further determines which type of the endoscopes the endoscope image is related to.

For example, the endoscope determination section 33 determines a mask pattern based on information such as pattern matching by edge extraction of the color video signal, and determines which type of the endoscopes the endoscope image is related to, for example, the first surgical endoscope 21, the second surgical endoscope 22, the first gastrointestinal endoscope 23, and the second gastrointestinal endoscope 24.

Then, the endoscope determination section 33 sends the determination result, that is, information indicating which type of the endoscopes the video signal inputted to the video signal input section 31 is related to, to the setting storage section 36.

On the other hand, when the color/monochrome determination section 32 determines that the video signal inputted to the video signal input section 31 is the monochrome video signal, that is, the monochrome video signal related to the interpretation image in the DICOM device 25, the information is sent to the setting storage section 36.

Each of the color/monochrome determination section 32, the endoscope determination section 33, and the setting storage section 36 may be partially configured of a processor using, for example, a CPU or an FPGA, and each of the sections may be operated and controlled according to a program stored in a memory (not shown) or may realize part or all of the functions with hardware electronic circuits.

For example, the endoscope determination section 33 may be configured of a first processor, the setting storage section 36 may be configured of a second processor, and the color/monochrome determination section 32 may be configured of a third processor.

The video processing section 34 to be described below may also be configured of a processor using, for example, a CPU or an FPGA, and may be operated and controlled according to a program stored in a memory (not shown).

Further, the color/monochrome determination section 32, the endoscope determination section 33, the video processing section 34, and the setting storage section 36 are configured of one processor, may be configured to realize functions of the first to third processors or a video processing function with the one processor, and may be configured using a CPU or an FPGA or may be configured of another electronic circuit as long as these functions are realized.

The setting storage section 36 has a function as a storage device that stores a plurality of display settings and also has a function as a processor (second processor) that selects a display setting corresponding to the endoscope image from the plurality of display settings. The setting storage section 36 can set in advance the set value (see FIG. 6) for each of "the video signals related to the different endoscope images", that is, for each of the video signals related to the first surgical endoscope 21, the second surgical endoscope 22, the first gastrointestinal endoscope 23, the second gastrointestinal endoscope 24, the DICOM device 25, and the recorder 26, which are previously shown as the medical modality related to the endoscope image in the present embodiment, and can store information related to these set values.

FIG. 6 illustrates an example of information stored in the setting storage section 36 in the medical display apparatus (the first monitor 11 or the second monitor 12).

The setting storage section 36 sends setting information corresponding to the video signal to the video processing section 34 in response to the determination results of the color/monochrome determination section 32 and the endoscope determination section 33, that is, in response to information indicating whether the video signal inputted to the video signal input section 31 is the video signal related to the DICOM device 25 or the video signal related to the first surgical endoscope 21, the second surgical endoscope 22, the first gastrointestinal endoscope 23, or the second gastrointestinal endoscope 24.

The video processing section 34 receives the setting information from the setting storage section 36 as described above, and performs video processing, which reflects the setting, on the video signal related to the endoscope image inputted to the video signal input section 31, thereby outputting the signal toward the display section 35.

The display section 35 is configured of a display panel including a liquid crystal panel, and displays the video signal that has been subjected to the predetermined video processing in the video processing section 34.

Operation of an Exemplary Embodiment

An operation of the medical display apparatus (the first monitor 11 or the second monitor 12) of the present embodiment will be described below with reference to FIG. 5 in which the type of the video signal related to the endoscope image inputted to the video signal input section 31 is determined and the video processing is performed, based on the determination result, on the inputted endoscope image with an optimal setting value.

Figure 5:
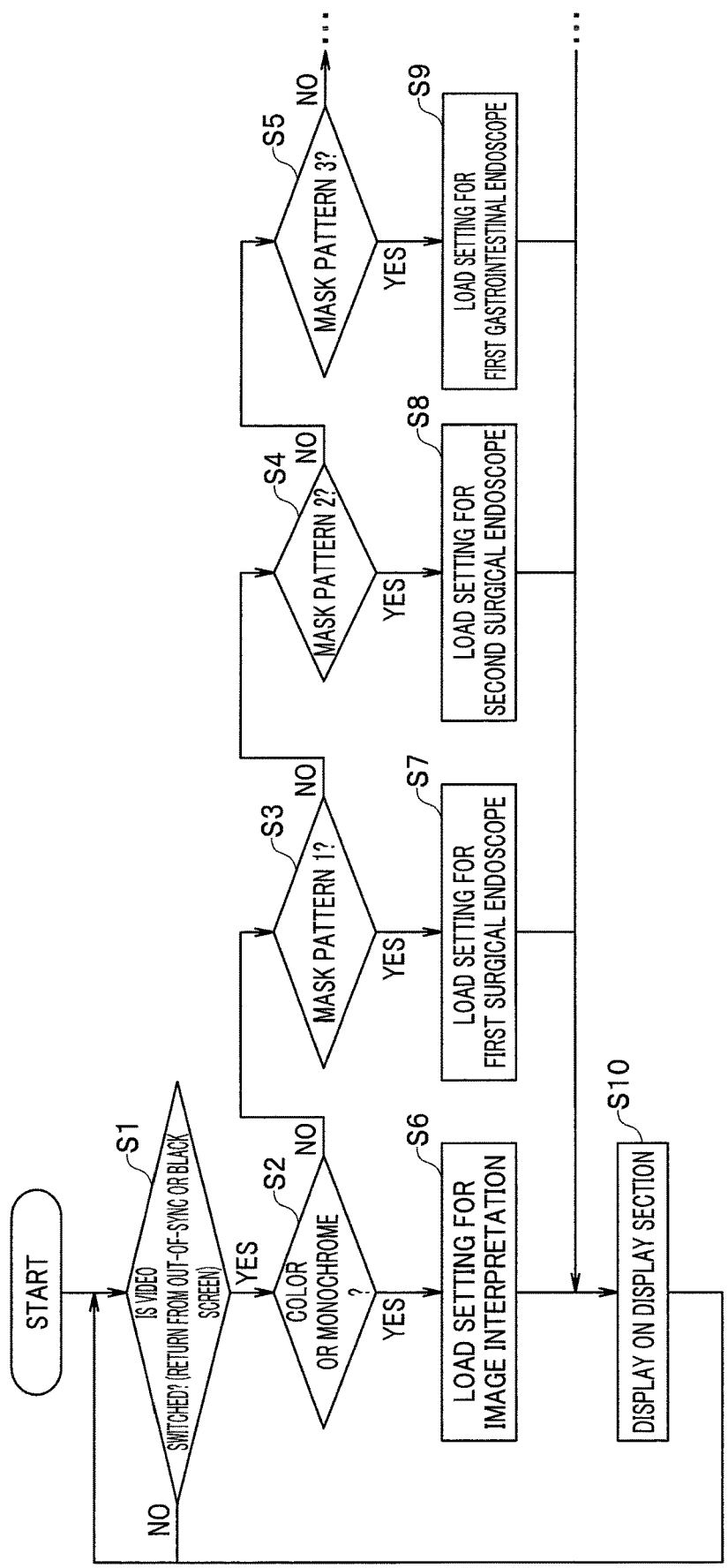
FIG. 5 is a flowchart showing an operation when an appropriate display setting is performed according to types of medical modalities in the medical display apparatus of an exemplary embodiment.

FIG. 5 is a flowchart showing an operation when an appropriate display setting is performed according to the type of medical modality in the medical display apparatus (the first monitor 11 or the second monitor 12).

In the endoscopic surgery system 1 according to the present embodiment, first, the video signals related to the endoscope images inputted from the respective medical modalities are appropriately routed by the switcher function in the system controller 3, and are sent to the first monitor 11 (or the second monitor 12).

Thus, when the first monitor 11 detects that the video signal switched appropriately in the system controller 3 is inputted (step S1), the first monitor 11 sends the inputted video signal to the color/monochrome determination section 32.

The color/monochrome determination section 32 determines whether the video signal inputted to the video signal input section 31 is either the color video signal or the monochrome video signal (step S2). In other words, the color/monochrome determination section 32 determines in step S2 whether the video signal inputted to the video signal input section 31 is the color video signal related to the image-pickup signal inputted from the endoscopes, for example, the first surgical endoscope 21, the second surgical endoscope 22, the first gastrointestinal endoscope 23, and the second gastrointestinal endoscope 24 or the monochrome video signal related to the interpretation image in the DICOM device 25.

When the color/monochrome determination section 32 determines in step S2 that the video signal inputted to the video signal input section 31 is the color video signal, the endoscope determination section 33 assumes that the video signal inputted to the video signal input section 31 is the video signal related to the image-pickup signal inputted from any one of the endoscopes, for example, the first surgical endoscope 21, the second surgical endoscope 22, the first gastrointestinal endoscope 23, and the second gastrointestinal endoscope 24 and determines which type of the endoscopes the endoscope image is related to (steps S3 to S5).

In other words, first, the endoscope determination section 33 determines, in step S3, a mask pattern based on information such as pattern matching by edge extraction of the color video signal, and determines whether the endoscope image is a mask pattern related to the first surgical endoscope 21.

In step S3, when the endoscope image is the mask pattern related to the first surgical endoscope 21, the endoscope determination section 33 sends the determination result to the setting storage section 36. In response to the determination result, the setting storage section 36 loads setting information corresponding to the first surgical endoscope 21 (step S7), and sends the loaded setting information to the video processing section 34.

When the setting information is received from the setting storage section 36, the video processing section 34 performs video processing, which reflects the setting, on the video signal related to the endoscope image inputted to the video signal input section 31 and outputs the signal toward the display section 35. Then, the display section 35 displays the video signal that has been subjected to the predetermined video processing in the video processing section 34 (step S10).

On the other hand, when the endoscope determination section 33 determines in step S3 that the endoscope image is not the mask pattern related to the first surgical endoscope 21, the endoscope determination section 33 determines whether the endoscope image is a mask pattern related to the second surgical endoscope 22 (step S4).

In step S4, when the endoscope image is the mask pattern related to the second surgical endoscope 22, the endoscope determination section 33 sends the determination result to the setting storage section 36, and the setting storage section 36 loads setting information corresponding to the second surgical endoscope 22 in response to the determination result (step S8) and sends the loaded setting information to the video processing section 34.

As in the above, the video processing section 34 performs video processing, which reflects the setting received from the setting storage section 36, on the video signal and outputs the signal toward the display section 35, and the display section 35 displays the video signal subjected to the predetermined video processing in the video processing section 34 (step S10).

Further, as in the above, when the endoscope image is the mask pattern related to the first gastrointestinal endoscope 23 (step S5), the endoscope determination section 33 sends the determination result to the setting storage section 36, and the setting storage section 36 loads setting information corresponding to the first gastrointestinal endoscope 23 in response to the determination result (step S9) and sends the loaded setting information to the video processing section 34.

As in the above, the video processing section 34 performs video processing, which reflects the setting received from the setting storage section 36, on the video signal and outputs the signal toward the display section 35, and the display section 35 displays the video signal subjected to the predetermined video processing in the video processing section 34 (step S10).

Although not shown in FIG. 5, the endoscope determination section 33 in the first monitor 11 also determines whether the video signal is related to the second gastrointestinal endoscope 24, and the video signal is appropriately subjected to video processing in the setting storage section 36 and the video processing section 34 in response to the determination result and is displayed on the display section 35.

On the other hand, when the color/monochrome determination section 32 determines that the video signal inputted to the video signal input section 31 is a monochrome video signal, that is, a monochrome video signal related to an interpretation image in the DICOM device 25 (step S2), the information is sent to the setting storage section 36.

The setting storage section 36 loads setting information corresponding to the DICOM device 25 in response to the determination result (step S6), and sends the loaded setting information to the video processing section 34.

When the setting information is received from the setting storage section 36, the video processing section 34 performs video processing, which reflects the setting, on the video signal related to the endoscope image (interpretation image) inputted to the video signal input section 31 and outputs the signal toward the display section 35. Then, the display section 35 displays the video signal subjected to the predetermined video processing in the video processing section 34 (step S10).

As described above, according to the medical display apparatus (the first monitor 11 or the second monitor 12), the video signal related to the endoscope image inputted to the video signal input section 31 is subjected to the color/monochrome determination in the color/monochrome determination section 32 and the endoscope type determination in the endoscope determination section 33, thereby the type of the medical modality corresponding to the video signal is determined. In addition, the set value information related to the endoscope image is loaded by the setting storage section 36 according to the determination result of the modality, whereby the medical display apparatus can display by performing a display setting optimal for the video signal on the medical modality even when the video signal input section 31 (the input terminal 31) is single and the inputted video signals related to the respective medical modalities have the same format (resolution).

Another exemplary embodiment will be described below.

Figure 7:
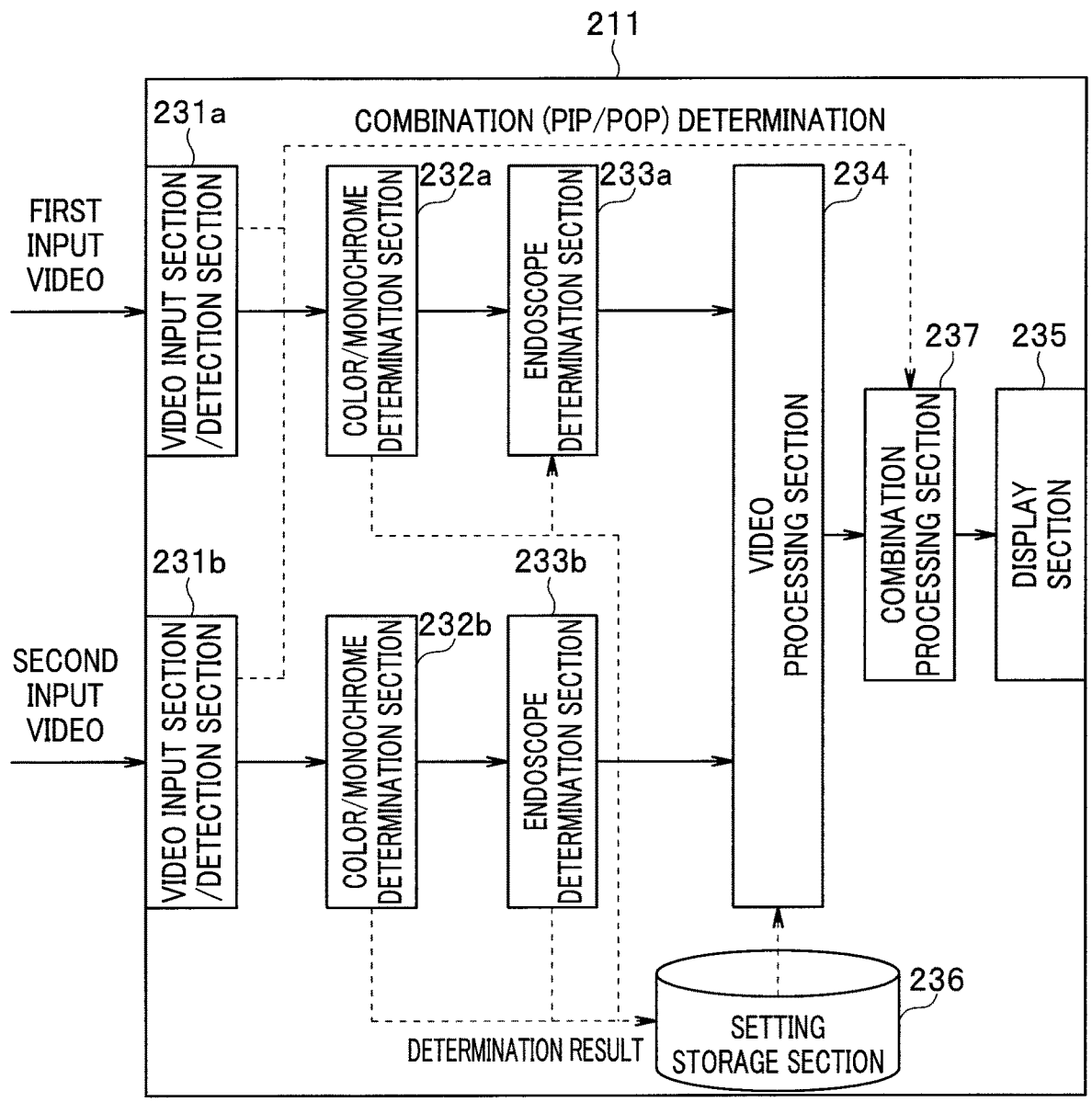
FIG. 7 is a block diagram showing an electrical configuration in a medical display apparatus according to an exemplary embodiment.
Figure 8:
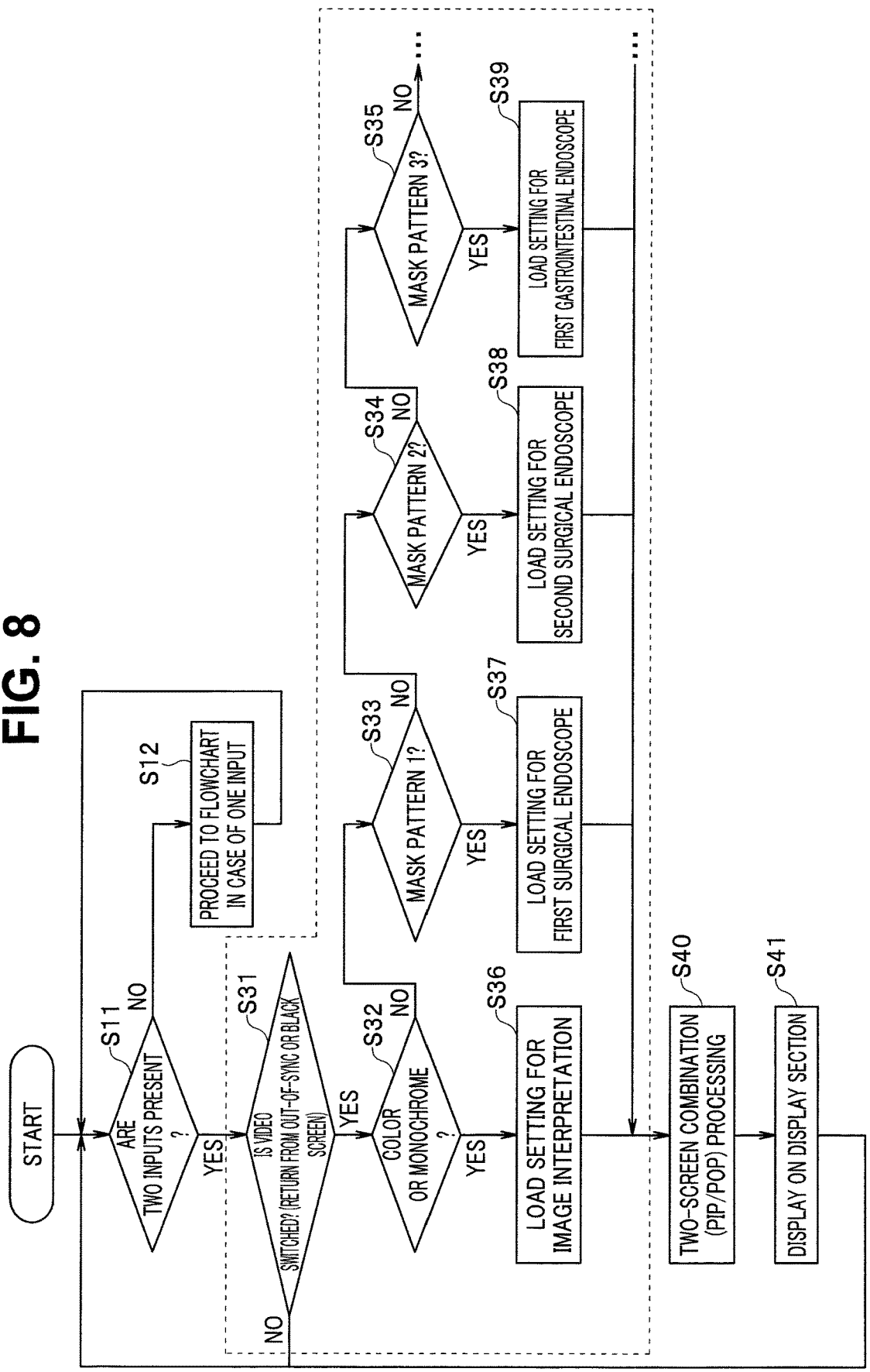
FIG. 8 is a flowchart showing an operation when an appropriate display setting is performed according to types of medical modalities in the medical display apparatus of an exemplary embodiment.

FIG. 7 is a block diagram showing an electrical configuration of a medical display apparatus according to an exemplary embodiment, and FIG. 8 is a flowchart showing an operation when an appropriate display setting is performed according to the type of modality in the medical display apparatus.

As in the endoscopic surgery system 1, an endoscopic surgery system including the medical display apparatus (a monitor 211) is a system including, for example, a medical instrument group 2, a system controller 3, a first surgical endoscope 21, a second surgical endoscope 22, a first gastrointestinal endoscope 23, and a second gastrointestinal endoscope 24.

As described above, only differences between the endoscopic surgery system of the present embodiment and the endoscopic surgery system will be described, and common components will not be described.

As in the first monitor 11 or the second monitor 12 in the endoscopic surgery system 1 (see FIG. 1), the monitor 211 according to the medical display apparatus is one of a plurality of monitors that hang from a ceiling to display an endoscope image under control of the system controller 3, and includes a plurality of video signal input sections (two video signal input sections) that perform a function similar to the function of the previously described video signal input section 31 in the medical display apparatus.

The monitor 211 includes a plurality of determination paths (two paths of a first determination path and a second determination path) including a color/monochrome determination section and an endoscope determination section that respectively perform functions similar to the functions of the color/monochrome determination section 32 and the endoscope determination section 33, with respect to video signals inputted to the respective video signal input sections.

The respective video signals passing through the plurality of determination paths are subjected to predetermined video processing by one video processing section, and then the respective video signals are appropriately subjected to combination processing by a combination processing section, which configures a combination processing circuit, and are displayed by one display section.

More specifically, as shown in FIG. 7, the monitor 211 includes one display section 235 that displays an endoscope image. Further, as described above, the monitor 211 includes two determination paths, and the first determination path includes: a video signal input section 231a to which a first video signal (a first inputted video signal) related to an endoscope image can be inputted from an external medical instrument; a video signal determination section (a color/monochrome determination section) 232a that determines the first video signal inputted to the video signal input section 231a; and an endoscope determination section 233a that determines an endoscope type based on the determination result of the color/monochrome determination section 232a.

On the other hand, in the monitor 211, the second determination path includes: a video signal input section 231b to which a second video signal (a second inputted video signal) related to an endoscope image can be inputted from an external medical instrument; a video signal determination section (a color/monochrome determination section) 232b that determines the second video signal inputted to the video signal input section 231b; and an endoscope determination section 233b that determines an endoscope type based on the determination result of the color/monochrome determination section 232b.

Here, each of the two video signal input sections 231a and 231b includes a video detector that also serves as a video detection section configured to determine whether the inputted video signal is a no-signal or a black image signal.

The monitor 211 further includes: a setting storage section 236 that is a setting storage section having a function similar to the function of the previously described setting storage section, and is capable of setting a set value for each of the first and second video signals related to different endoscope images; and a video processing section 234 that generates a video obtained by reflecting the setting of the setting storage section 236 for each of the determined first and second video signals, according to the determination results of the color/monochrome determination section 232a and the endoscope determination section 233a or the determination results of the color/monochrome determination section 232b and the endoscope determination section 233b.

The video processing section 234 receives signals outputted from the two endoscope type determination sections 233a and 233b in the two determination paths to generate a video reflecting a predetermined set value stored in the setting storage section 236, and outputs the video to a subsequent stage.

On the other hand, the monitor 211 includes a combination processing section 237 subsequent to the video processing section 234 to perform combination processing on the two inputted video signals based on signals detected by the two video signal input sections 231a and 231b.

As described above, the monitor 211 includes the two video signal input sections 231a and 231b, but each of the video signal input sections 231a and 231b is configured as an input terminal that independently performs a function similar to the function of the video signal input section 31.

In other words, each of the video signal input section 231a and the video signal input section 231b inputs the endoscope image (the first inputted video signal or the second inputted video signal) routed appropriately by a switcher function in the system controller 3.

In addition, as described above, the video signal input section 231a and the video signal input section 231b have a function of detecting that the video signal (the first inputted video signal or the second inputted video signal) is inputted, and also detect whether the inputted video signal is switched by the switcher function in the system controller 3.

The color/monochrome determination section 232a has a function of determining whether the first inputted video signal inputted to the video signal input section 231a is either a color video signal or a monochrome video signal. On the other hand, the color/monochrome determination section 232b also has a function of determining whether the second inputted video signal inputted to the video signal input section 231b is either a color video signal or a monochrome video signal.

In other words, each of the color/monochrome determination section 232a and the color/monochrome determination section 232b determines whether the inputted video signal is a color video signal related to the image-pickup signal inputted from the endoscopes, for example, the first surgical endoscope 21, the second surgical endoscope 22, the first gastrointestinal endoscope 23, and the second gastrointestinal endoscope 24 or a monochrome video signal related to the interpretation image in the DICOM device 25.

When the color/monochrome determination section 232a determines that the video signal is the color video signal based on the determination result, the endoscope determination section 233a recognizes that the video signal inputted to the video signal input section 231a is the video signal related to the image-pickup signal inputted from any one of the endoscopes, for example, the first surgical endoscope 21, the second surgical endoscope 22, the first gastrointestinal endoscope 23, and the second gastrointestinal endoscope 24 and further determines which type of the endoscopes the endoscope image is related to.

As in the above, when the color/monochrome determination section 232b determines that the video signal is the color video signal based on the determination result, the endoscope determination section 233b recognizes that the video signal inputted to the video signal input section 231b is the video signal related to the image-pickup signal inputted from any one of the endoscopes, for example, the first surgical endoscope 21, the second surgical endoscope 22, the first gastrointestinal endoscope 23, and the second gastrointestinal endoscope 24 and further determines which type of the endoscopes the endoscope image is related to.

Also each of the endoscope determination section 233a and the endoscope determination section 233b sends the determination result, that is, information indicating which type of the endoscopes the inputted video signal is related to, to the setting storage section 236.

On the other hand, when the color/monochrome determination section 232a or the color/monochrome determination section 232b determines that the inputted video signal is the monochrome video signal, that is, the monochrome video signal related to the interpretation image in the DICOM device 25, the information is sent to the setting storage section 236.

The setting storage section 236 can set in advance the set value (see FIG. 6) for each of "the video signals related to the different endoscope images", that is, for each of the video signals related to the first surgical endoscope 21, the second surgical endoscope 22, the first gastrointestinal endoscope 23, the second gastrointestinal endoscope 24, the DICOM device 25, and the recorder 26, which are previously shown as the medical modality related to the endoscope image in the present embodiment, and can store information related to these set values.

Then, the setting storage section 236 sends setting information corresponding to the video signal to the video processing section 234 in response to the determination results of the color/monochrome determination section 232a and the color/monochrome determination section 232b and the endoscope determination section 233a and the endoscope determination section 233b, that is, in response to information indicating whether the inputted video signal is the video signal related to the DICOM device 25 or the video signal related to the first surgical endoscope 21, the second surgical endoscope 22, the first gastrointestinal endoscope 23, or the second gastrointestinal endoscope 24.

The video processing section 234 also receives the setting information from the setting storage section 236, and performs video processing, which reflects the setting, on the first inputted video signal or the second inputted video signal inputted to the video signal input section 231a or the video signal input section 231b, thereby outputting the signal toward the combination processing section 237 of the subsequent stage.

As described above, the combination processing section 237 performs combination processing, for example, PIP/POP processing on the two inputted video signals, based on the signals detected by the two video signal input sections 231a and 231b, that is, the signals related to the detection result indicating whether the inputted video signal is a no-signal or a black image signal.

The display section 235 is configured of a display panel including a liquid crystal panel, and displays the video signal that has been subjected to the predetermined video processing in the video processing section 234 and subjected to the combination processing in combination processing section 237.

Operation of Another Exemplary Embodiment

An operation of the medical display apparatus (the monitor 211) of the present embodiment will be described below with reference to FIG. 8 in which the type of the video signal (the first inputted video signal or the second inputted video signal) related to the endoscope image inputted to the video signal input section 231a or the video signal input section 231b is determined and the video processing is performed, based on the determination result, on the inputted endoscope image with an optimal setting value.

Also in the endoscopic surgery system 1 first, the video signals related to the endoscope images inputted from the respective medical modalities are appropriately routed by the switcher function in the system controller 3, and are sent to the video signal input section 231a and the video signal input section 231b in the monitor 211.

First, the monitor 211 detects the presence or absence of the respective inputted video signals in the video signal input section 231a and the video signal input section 231b (step S11). When the video signal is inputted to only one of the input sections (step S12), a processing flow similar to the processing flow shown in FIG. 5 is performed only in the discrimination path corresponding to the video signal input section to which the video signal is inputted.

On the other hand, when a predetermined video signal is inputted to both of the video signal input section 231a and the video signal input section 231b in step S11, the input of the video signal appropriately switched by the system controller 3 is detected (step S31), and the video signal input section 231a and the video signal input section 231b send the inputted video signals to the color/monochrome determination section 232a and the color/monochrome determination section 232b, respectively.

Then, the color/monochrome determination section 232a and the color/monochrome determination section 232b determine in the respective determination paths whether the inputted video signal is either a color video signal or a monochrome video signal (step S32). When the color/monochrome determination section 232a and the color/monochrome determination section 232b in the endoscope determination section 33 determine in step S32 that the video signal is the color video signal, the endoscope determination section 33 assumes that the inputted video signal is the video signal related to the image-pickup signal inputted from any one of the endoscopes, for example, the first surgical endoscope 21, the second surgical endoscope 22, the first gastrointestinal endoscope 23, and the second gastrointestinal endoscope 24 and determines which type of the endoscopes the endoscope image is related to (steps S33 to S35).

In other words, first, the endoscope determination section 233a or the endoscope determination section 233b determines, in step S33, a mask pattern based on information such as pattern matching by edge extraction of the color video signal, and determines whether the endoscope image is a mask pattern related to the first surgical endoscope 21.

In step S33, when the endoscope image is the mask pattern related to the first surgical endoscope 21, the endoscope determination section 233a or the endoscope determination section 233b sends the determination result to the setting storage section 236. In response to the determination result, the setting storage section 236 loads setting information corresponding to the first surgical endoscope 21 (step S37), and sends the loaded setting information to the video processing section 234.

When the setting information is received from the setting storage section 236, the video processing section 234 performs video processing, which reflects the setting, on the video signal related to the endoscope image inputted to the video signal input section 231a or the video signal input section 231b and outputs the signal toward the combination processing section 237.

Then, the combination processing section 237 performs a predetermined combination processing (for example, PIP/POP processing) on the video signals related to the two screens outputted from the video processing section 234, and sends the video signals to the display section 235 (step S40).

The display section 235 displays the video signals subjected to the predetermined combination processing in the combination processing section 237 (step S41).

On the other hand, when the endoscope determination section 233a or the endoscope determination section 233b determines in step S33 that the endoscope image is not the mask pattern related to the first surgical endoscope 21, the endoscope determination section 233a or the endoscope determination section 233b determines whether the endoscope image is a mask pattern related to the second surgical endoscope 22 (step S34).

In step S34, when the endoscope image is the mask pattern related to the second surgical endoscope 22, the endoscope determination section 233a or the endoscope determination section 233b sends the determination result to the setting storage section 236, and the setting storage section 236 loads setting information corresponding to the second surgical endoscope 22 in response to the determination result (step S38) and sends the loaded setting information to the video processing section 234.

As in the above, the video processing section 234 performs video processing, which reflects the setting received from the setting storage section 236, on the video signal and outputs the signal toward the combination processing section 237, the video signal is appropriately subjected to combination processing in the combination processing section 237, and then the display section 235 displays the video signal subjected to the combination processing (steps S40 and S41).

Further, as in the above, when the endoscope image is the mask pattern related to the first gastrointestinal endoscope 23 (step S35), the setting storage section 236 loads setting information corresponding to the first gastrointestinal endoscope 23 (step S39) as described above and sends the loaded setting information to the video processing section 234.

As in the above, the video processing section 234 performs video processing, which reflects the setting received from the setting storage section 236, on the video signal and outputs the signal toward the combination processing section 237, the video signal is appropriately subjected to combination processing in the combination processing section 237, and then the display section 235 displays the video signal subjected to the combination processing (steps S40 and S 41).

Although not shown in FIG. 8, the endoscope determination section 233a and the endoscope determination section 233b in the monitor 211 also determine whether the video signal is related to the second gastrointestinal endoscope 24, and the video signal is appropriately subjected to video processing in the setting storage section 236, the video processing section 234, and the combination processing section 237 in response to the determination result and is displayed on the display section 235.

On the other hand, when the color/monochrome determination section 232a or the color/monochrome determination section 232b determines that the video signal inputted to the video signal input section 231a or the video signal input section 231b is a monochrome video signal, that is, a monochrome video signal related to an interpretation image in the DICOM device 25 (step S32), the information is sent to the setting storage section 236.

The setting storage section 236 loads setting information corresponding to the DICOM device 25 in response to the determination result (step S36), and sends the loaded setting information to the video processing section 234.

When the setting information is received from the setting storage section 236, the video processing section 234 performs video processing, which reflects the setting, on the video signal related to the endoscope image (interpretation image) inputted to the video signal input section 231a or the video signal input section 231b and outputs the signal toward the combination processing section 237 and the display section 235. Then, the video signal is subjected to the appropriate combination processing in the combination processing section 237, and the display section 235 displays the video signal subjected to the processing (steps S40 and S41).

As described above, the medical display apparatus (monitor 211) includes: the input section (the video signal input section 231a or the video signal input section 231b) that plays a role similar to the processing path including the video signal input section 31, the color/monochrome determination section 32, and the endoscope determination section 33; and the plurality of paths including the determination path (the color/monochrome determination section 232a, the color/monochrome determination section 232b, the endoscope determination section 233a, and the endoscope determination section 233b) corresponding to such the video signal input sections. The respective input sections and the paths including the determination path play a role similar to that described previously, and the endoscope images inputted to the respective video signal input sections can be combined and displayed.

Note that the present invention is not limited to the embodiments described above, and various changes and modifications can be made without departing from the scope of the present invention.

What is claimed is:

1. A medical display apparatus comprising:
a display configured to display an endoscope image, the endoscope image including a mask pattern;
at least one video signal input circuit wherein a plurality of video signals related to the endoscope image are configured to be input to the at least one video signal input circuit from an external medical instrument;
a video processing circuit configured to generate a video reflecting a display setting specified for each of the video signals;
a first processor; and
a second processor, wherein:
the first processor is configured to determine an endoscope type based on the mask pattern of the endoscope image;
the second processor designates a display set value for each video image for the video processing circuit based on the determination of the endoscope type, each video image being related to a different endoscope image; and
the mask pattern being determined based on pattern matching by edge extraction of one of the video signals.

2. The medical display apparatus according to claim 1, further comprising:
a video detector configured to determine whether an input is a no-signal or a black image signal; and
when a plurality of videos is detected, a combination processing circuit configured to combine the plurality of videos into multiple screen displays, wherein:
the second processor is configured to designate an appropriate display set value for the video processing circuit in each of the multiple screen displays.

3. The medical display apparatus according to claim 1, wherein
the video signals input to the video signal input circuit are video signals of a same video format transmitted in a same transmission standard.

4. The medical display apparatus according to claim 1, further comprising:
a third processor configured to determine whether the video signals input to the video signal input circuit are color video signals or monochrome video signals, wherein:
when the video signals are the color video signals based on a determination result in the third processor, the first processor determines the endoscope type based on the mask pattern of the endoscope image;
the video processing circuit generates a video reflecting a display setting of the second processor for each of the determined video signals, according to the determinations of the first and third processors; and
when the video signals are monochrome video signals based on the determination result in the third processor, information is sent to a setting storage section.

5. The medical display apparatus according to claim 1, wherein:
a video signal related to at least one: endoscope image of an interpretation image, a plurality of surgical endoscope images, or a plurality of gastrointestinal endoscopes is input to the video signal input circuit, and
the second processor is configured to designate a display set value for each of the video signals input to the video signal input circuit, based on a determination of the first processor.

6. An endoscopic surgery system comprising:
a controlled instrument that includes a plurality of medical instruments; and
a medical display apparatus including:
a display configured to display an endoscope image that includes a mask pattern;
at least one video signal input circuit wherein a plurality of video signals related to the endoscope image are configured to be input from one of the plurality of medical instruments;
a third processor configured to determine whether the video signals input to the video signal input circuit are color video signals or monochrome video signals;
when the third processor determines that the video signals are the color video signals, a first processor configured to determine an endoscope type based on the mask pattern of the endoscope image, the mask pattern being determined based on pattern matching by edge extraction of one of the video signals;
a video processing circuit configured to generate a video reflecting a display setting for each of the video signals based on the determination results of the first and third processors; and
a second processor configured to designate a display set value for each video image for the video processing circuit based on the determination of the endoscope type, each video image being related to a different endoscope image.

7. A method of displaying a medical image, comprising:
performing a first determination of determining whether video signals related to an endoscope image among video signals inputted to a video signal input circuit from an external medical instrument are color video signals or monochrome video signals,
performing a second determination of determining an endoscope type based on a mask pattern of the endoscope image when the video signals are the color video signals, the mask pattern being determined based on pattern matching by edge extraction of one of the video signals; and
generating a video reflecting a display setting for each of the determined video signals, according to results of the first and second determinations.

* * * * *